(12) United States Patent
Smith et al.

(10) Patent No.: US 6,974,447 B2
(45) Date of Patent: Dec. 13, 2005

(54) HIGH GAS BARRIER RECEPTACLE AND CLOSURE ASSEMBLY

(75) Inventors: Sidney T. Smith, Lake Forest, IL (US); Larry Rosenbaum, Gurnee, IL (US); Gregg Nebgen, Burlington, WI (US); William S. Hurst, Burlington, WI (US); William S. Hoerle, Lindenhurst, IL (US); Adel M. Sadik, Fox River Grove, IL (US); Melissa J. Skelnik, Wonder Lake, IL (US); Steven H. Giovanetto, Vernon Hills, IL (US); Bradley Buchanan, Ross, CA (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 344 days.

(21) Appl. No.: 10/124,599

(22) Filed: Apr. 16, 2002

(65) Prior Publication Data

US 2003/0109847 A1    Jun. 12, 2003

Related U.S. Application Data

(60) Provisional application No. 60/284,277, filed on Apr. 17, 2001.

(51) Int. Cl.[7] .................. A61B 19/00; A61M 37/00; B65D 30/08; B65D 37/00; B29D 22/00
(52) U.S. Cl. .................. 604/415; 604/403; 604/6.15; 604/905; 383/94; 383/109; 383/113; 128/912; 128/DIG. 24; 220/62.21; 222/212; 206/828; 428/35.2; 428/35.4
(58) Field of Search ................ 604/4.01, 6.15, 604/6.16, 403, 408–416; 128/897–898, 912, 128/DIG. 24; 222/206–215, 519–521, 541.1, 222/541.6, 541.7, 544, 562, 563, 566, 572; 383/210–211, 383/38, 42, 59, 66, 67

(56) References Cited

U.S. PATENT DOCUMENTS 3,882,259 A * 5/1975 Nohara et al. ............. 428/36.7

(Continued)

FOREIGN PATENT DOCUMENTS

EP    0 561 428 A1    2/1987

(Continued)

OTHER PUBLICATIONS

Eval®Resin F100A Paper.

(Continued)

*Primary Examiner*—Patricia Bianco

(74) *Attorney, Agent, or Firm*—Senniger Powers

(57) ABSTRACT

The present invention provides a receptacle for a therapeutic fluid susceptible to deterioration on exposure to a gas such as oxygen or carbon dioxide. The receptacle has walls of sheet material each including at least one layer forming a barrier essentially impermeable to such gas, and a seal sealing the walls together in a region thereof. A transfer tube is sealed in the seal having a proximal end in the receptacle, a distal end accessible from outside the receptacle, a flow passage extending between said proximal and distal ends, and a closure blocking flow through the flow passage adapted to be pierced by a tubular needle for transfer of therapeutic through the needle. The transfer tube and closure are essentially impermeable to said gas.

56 Claims, 5 Drawing Sheets

U.S. PATENT DOCUMENTS

| | | | |
|---|---|---|---|
| 4,254,169 A | 3/1981 | Schroeder | |
| 4,284,674 A | 8/1981 | Sheptak | |
| 4,361,628 A | 11/1982 | Krueger et al. | |
| 4,561,110 A | 12/1985 | Herbert | |
| 4,647,483 A | 3/1987 | Tse et al. | |
| 4,699,816 A | 10/1987 | Galli | |
| 4,826,955 A | 5/1989 | Akkapeddi et al. | |
| 4,837,084 A * | 6/1989 | Warren | 428/349 |
| 4,857,409 A | 8/1989 | Hazelton et al. | |
| 4,917,925 A | 4/1990 | Loretti et al. | |
| 5,004,647 A | 4/1991 | Shah | |
| 5,164,258 A | 11/1992 | Shida et al. | |
| 5,232,754 A | 8/1993 | Waugh | |
| 5,234,903 A | 8/1993 | Nho et al. | |
| 5,352,773 A * | 10/1994 | Kandler et al. | 530/385 |
| 5,929,031 A | 7/1999 | Kerwin et al. | |
| 6,083,587 A | 7/2000 | Smith | |
| 6,213,996 B1 | 4/2001 | Jepson et al. | |
| 6,217,351 B1 | 4/2001 | Fung et al. | |
| 6,217,568 B1 | 4/2001 | Jepson et al. | |
| 6,221,470 B1 * | 4/2001 | Ciocca et al. | 428/218 |
| 6,287,289 B1 * | 9/2001 | Niedospial, Jr. | 604/408 |
| 6,288,027 B1 | 9/2001 | Gawryl et al. | |
| 6,344,033 B1 | 2/2002 | Jepson et al. | |
| 6,468,377 B1 * | 10/2002 | Sperko et al. | 156/229 |
| 6,652,942 B2 * | 11/2003 | Ling et al. | 428/36.91 |
| 6,743,523 B1 * | 6/2004 | Woo et al. | 428/516 |

FOREIGN PATENT DOCUMENTS

| | | |
|---|---|---|
| EP | 0 451 977 A1 | 3/1991 |
| EP | 0 504 808 A1 | 3/1992 |
| EP | 0 698 487 A1 | 3/1995 |
| EP | 0 465 681 A1 | 1/1999 |
| GB | 2 131 739 A | 9/1983 |

OTHER PUBLICATIONS

Irvine Scientific Promotional Materials.
Mediatech Inc. Promotional Materials.
JRH Biosciences Promotional Materials.
BioWhittaker, Inc. Promotional Materials.
Sigma Promotional Materials.
Wave Biotech Promotional Materials.
American Fluoroseal Corporation Promotional Materials.
Ethox Corp. Promotional Materials.
FMI, Inc. Promotional Materials.
Newport Biosystems Promotional Materials.
Charter Medical Promotional Materials.
TCTECH Promotional Materials.
HyClone Promotional Materials.
Stedim Promotional Materials.
Bio-Polymers, Inc. Promotional Materials.

* cited by examiner

FIG.1a
FIG.1b
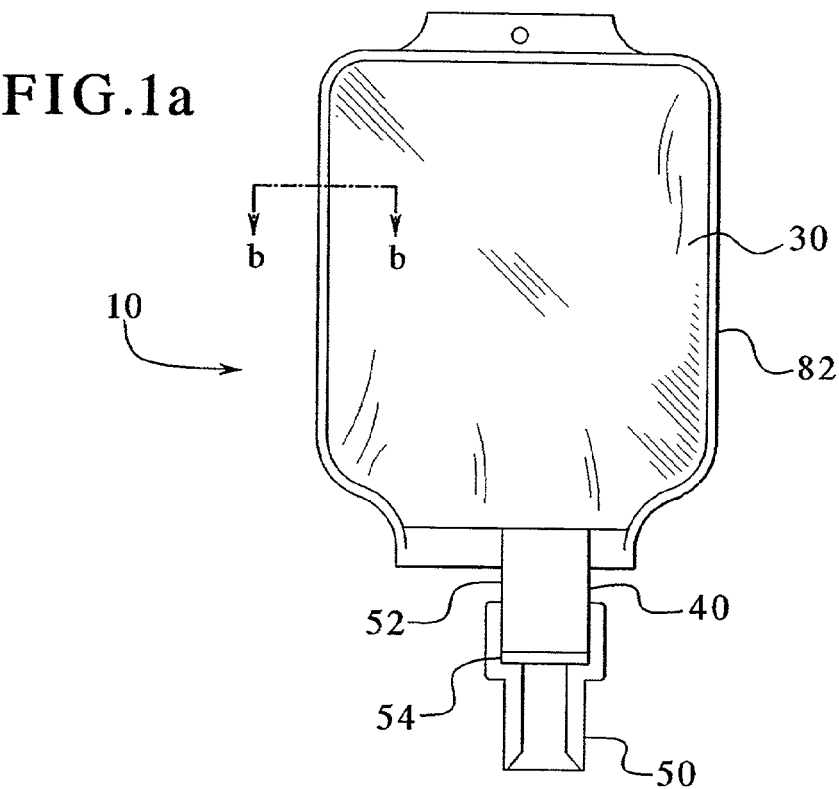
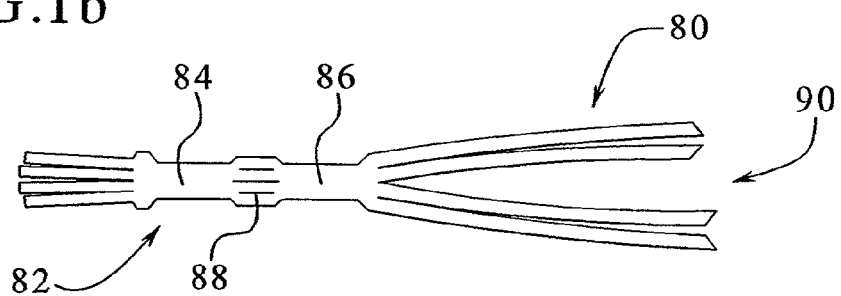

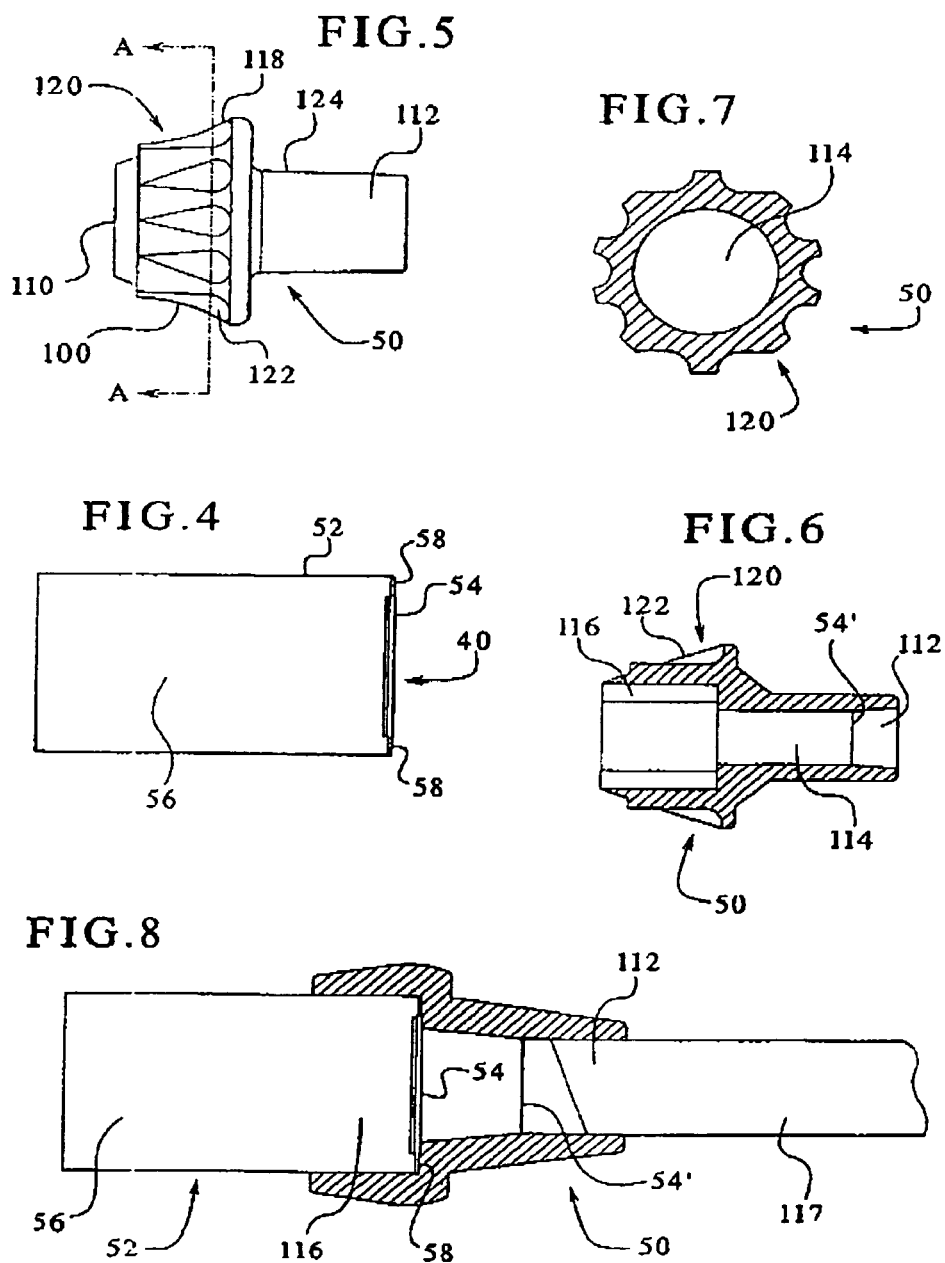

HIGH GAS BARRIER RECEPTACLE AND CLOSURE ASSEMBLY

CROSS-REFERENCE TO RELATED APPLICATIONS

This application claims the benefit of provisional application Ser. No. 60/284,277, filed Apr. 17, 2001, which is incorporated by reference and made a part hereof.

TECHNICAL FIELD

The present invention relates to a high gas barrier primary receptacle system, and more particularly to a receptacle system for medical solutions.

BACKGROUND OF THE INVENTION

There is an ever increasing number of therapeutic fluids being developed for delivery by a flexible receptacle. Many of these therapeutic fluids are sensitive as they degrade or react with gases such as oxygen and carbon dioxide. These therapeutic fluids must be protected from contact by such gases to maintain the efficacy of the therapeutic fluid.

For example, hemoglobin solutions are known to lose their ability to function as blood substitutes during storage. A hemoglobin solution loses its ability to function as a blood substitute because of spontaneous transformation of oxyhemoglobin in the solution to methemoglobin, a physiologically inactive form of hemoglobin which does not function as a blood substitute by releasing oxygen into a patient's bloodstream. To improve shelf life, the blood substitutes industry delays loss of function by refrigerating or freezing the solutions, or controlling the oxygenation state of the hemoglobin within the solution.

Therapeutic hemoglobin solutions are typically oxygenated, stored frozen in conventional oxygen-permeable, 200 ml plastic solution bags, and thawed to room temperature hours before use.

WO 99/15289 describes a multiple layer structure for fabricating medical products. The layer structure has a core layer of an ethylene vinyl alcohol copolymer, a solution contact layer of a polyolefin positioned on a first side of the core layer, an outer layer positioned on a second side of the core layer opposite the solution contact layer, the outer layer being selected from the group consisting of polyamides, polyesters and polyolefins, and a tie layer on each side of the core layer. The tie layer is 0.2–1.2 mils in thickness, and is the only layer of the structure which may be composed of ethylene vinyl acetate.

U.S. Pat. No. 6,271,351 describes a method of storing deoxyhemoglobin in a container which is said to exhibit low oxygen permeability. The container is composed of a layered structure including ethylene vinyl alcohol, but does not include ethylene vinyl acetate.

There is a need for containers having minimal oxygen permeability which would enable deoxygenated hemoglobin solutions to be stored for weeks or months at room temperature and then used as a blood substitute.

Receptacles used for the shipping, storing, and delivery of liquids, such as medical or therapeutic fluids, are often fabricated from single-ply or multiple-ply polymeric materials. Two sheets of these materials are placed in overlapping relationship and the overlapping sheets are bonded at their outer peripheries to define a chamber or pouch for containing liquids. It is also possible to extrude these materials as a tube and to seal longitudinally spaced portions of the tube to define chambers between two adjacent seals. Typically, the materials are joined along their inner surfaces using bonding techniques such as heat sealing, radio-frequency sealing, thermal transfer welding, adhesive sealing, solvent bonding, sonic sealing, and laser welding.

It is also common to provide such receptacles with access ports to provide access to the interior of the receptacle. Access ports typically take the form of one or more end ports (transfer tubes) inserted between the sidewalls of the receptacle or panel ports attached to a sidewall of the receptacle. The end ports typically have a fluid passageway with a closure wall positioned inside the passageway to form a fluid tight seal of the receptacle. The closure, typically in the form of a membrane, must be punctured by an access needle or "spike" to allow for delivery of the contents of the receptacle.

Conventional flexible solution receptacles employing end port designs typically use flexible PVC or soft polyolefins such as LDPE to construct the port tubes. Such materials have sufficient elasticity to grip the outside of an access spike to retain the spike during fluid delivery. The inner diameter of the end ports are dimensioned to be smaller than the outer diameter of the access device. Due to the ductility of PVC or LDPE, the port tube can expand about the outside of the access spike to form an interference fit therewith. However, such receptacle and port closure systems are readily permeated by oxygen and other gases such as carbon dioxide. If such receptacles are to be utilized to house a gas sensitive liquid, such packages must utilize a gas barrier overwrap material.

To provide a stand-alone gas barrier primary receptacle, all components of the receptacle system should be fabricated using barrier material. For medical applications where such receptacles are typically disposed of by incineration, it is desirable to construct the receptacle system components from non-halogen containing polymers. Halogen containing compounds have the potential for creating inorganic acids upon incineration. Further, for medical applications, it is also desirable to construct the receptacle system components from polymers having a low quantity of low molecular weight additives, such as plasticizers, as such low molecular weight components can potentially leach out into the fluids contained or transported therein.

It is well known that certain materials provide a high resistance to the ingress of oxygen or other gases. For example, ethylene vinyl alcohol (EVOH) provides a high barrier to the ingress of oxygen. However, EVOH provides a significant design challenge for use in flexible receptacle systems as EVOH is also know to be a very rigid material. A port tube containing a significant quantity of EVOH will have insufficient elasticity to expand around an access device. Thus, such an EVOH containing port tube cannot be dimensioned to be smaller in diameter than an access device.

Due to the variation in the outer diameter dimensions of access devices commercially, it is also difficult to design a single port tube to have an appropriate diameter to form an interference fit with all access devices commercially available. The spike holder or needle holder has sufficient elasomeric properties to form around an access device and form a grasping hold of the access device. The present invention is provided to solve these and other problems.

SUMMARY OF THE INVENTION

The present invention provides a receptacle for a therapeutic fluid susceptible to deterioration on exposure to a gas such as oxygen or carbon dioxide. The receptacle has walls of sheet material each including at least one layer forming a barrier essentially impermeable to said gas, and a seal sealing the walls together in a region thereof. A transfer tube is sealed in the seal having a proximal end in the receptacle, a distal end accessible from outside the receptacle, a flow passage extending between said proximal and distal ends, and a closure blocking flow through said flow passage adapted to be pierced by a tubular needle for transfer of therapeutic through the needle. The transfer tube and closure are essentially impermeable to said gas.

The present invention further provides a transfer tube for attachment to a receptacle adapted to hold a fluent therapeutic susceptible to deterioration on exposure to gas such as oxygen or carbon dioxide. The transfer tube has a tubular body having a proximal end, a distal end opposite the proximal end, a flow passage extending between said proximal and distal ends adapted to communicate with said receptacle, and a closure blocking flow through the flow passage and adapted to be pierced by a tubular needle for transfer of therapeutic through the needle. The tubular body and closure are essentially impermeable to said gas.

The present invention is also directed to a needle holder for application to the distal end of a transfer tube of a receptacle particularly adapted to hold a fluent therapeutic susceptible to deterioration on exposure to gas such as oxygen or carbon dioxide. The needle holder is adapted to hold in place the carrier of a transfer needle with the needle piercing the transfer tube. The holder has a body having a first annular wall defining a first cavity at a first end of the body, a second annular wall defining a second cavity at a second end of the body, and a flow passage extending between the two cavities, the first annular wall being sized for an interference fit with said transfer tube to releasably attach the needle holder to the transfer tube, and the second annular wall being sized for an interference fit with said needle carrier to releasably attach the needle carrier to the needle holder in a position in which needle is disposed in said flow passage.

Additional features, advantages, and other aspects and attributes of the present invention will be discussed with reference to the following drawings and accompanying specification.

BRIEF DESCRIPTION OF THE DRAWINGS

FIG. 1a is a plan view of a flowable materials receptacle and closure system;

FIG. 1b is a cross-sectional view taken along line b—b of FIG. 1a;

FIG. 4 is a cross-sectional view of a membrane film and tube assembly;

FIG. 5 is a side view of a needle or "spike" holder;

FIG. 6 is cross-sectional view of the spike holder of FIG. 6;

FIG. 7 is an cross-sectional view taken along line A—A of FIG. 6;

FIG. 8 is an assembly of the membrane film and tube assembly with the spike holder or needle holder of FIG. 5 with a spike being introduced therein.

DETAILED DESCRIPTION OF THE INVENTION

Figure 1C:
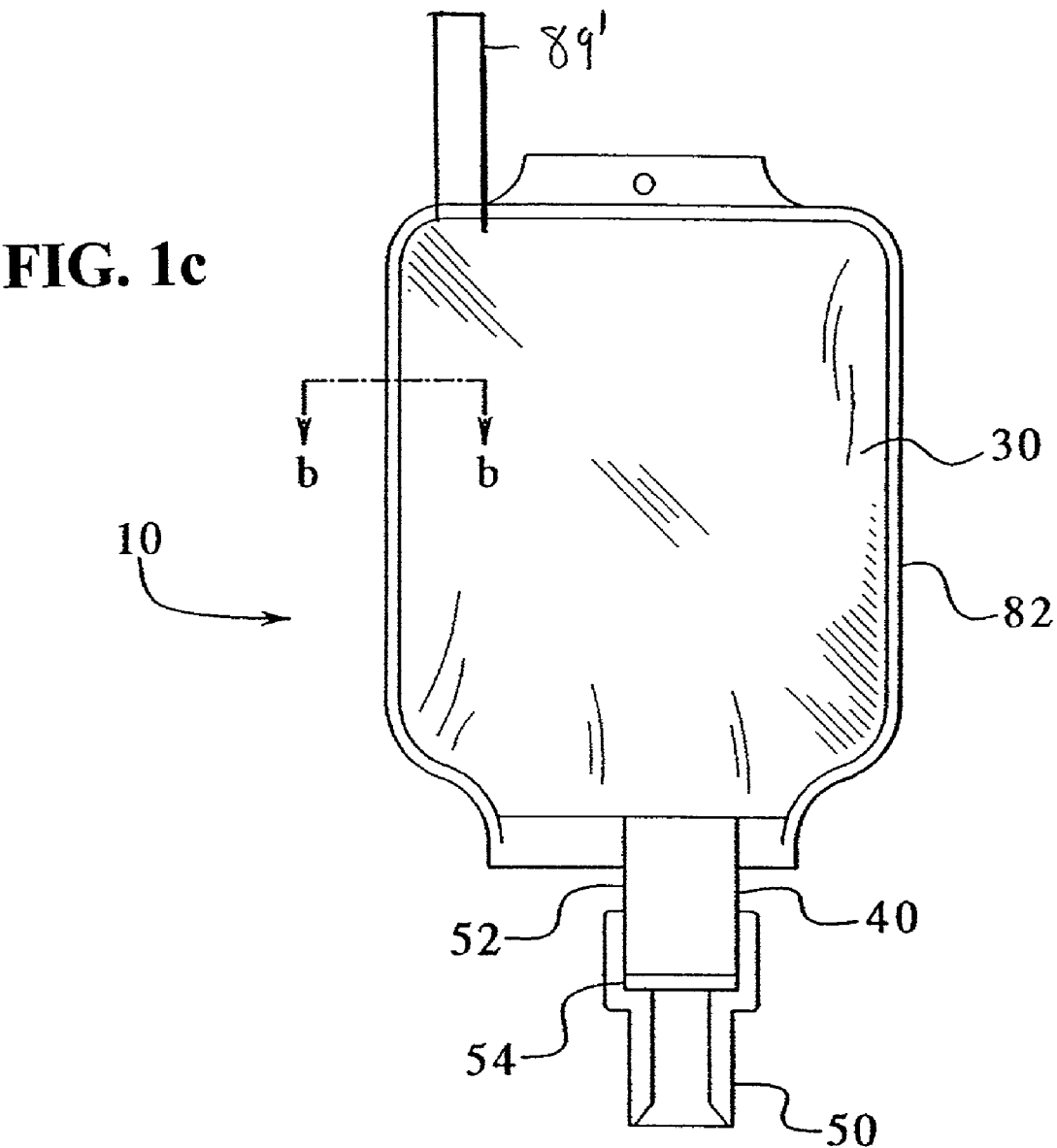
FIG. 1c is a plan view of a flowable materials receptacle having a fill port and an administration port.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 1a shows a flowable materials receptacle and closure system generally referred to as 10. The system includes a flowable materials receptacle 30, a port (transfer) tube and closure assembly 40, and a needle or "spike" holder 50. The relative size of the receptacle 30, assembly 40, and spike holder 50 are exaggerated for illustrative purposes. In a preferred form of the invention, the system 10 is useful for containing and delivering a fluent therapeutic susceptible to deterioration on exposure to a gas such as oxygen or carbon dioxide. The system is also particularly well suited for storage and delivery of a buffered solution.

What is meant by "flowable material" is a material that will flow by the force of gravity. Flowable materials therefore include both liquid items and powdered or granular items and the like. Flowable materials receptacles find particular use for storage and delivery of medical or therapeutic fluids and include, but are not limited to, I.V. receptacles, peritoneal dialysis drain and fill receptacles, blood receptacles, blood product receptacles, blood substitute receptacles, nutritional receptacles, food receptacles and the like.

FIGS. 1a and 8 illustrate the assembly 40 as including a port (transfer) tube 52 and a closure in the form of a wall or membrane 54. The port tube 52 defines a fluid flow passage 56 and has an end surface 58. The membrane 54 is shown attached to the port tube end surface 58. It is contemplated by the present invention the membrane 54 could also be positioned inside the port tube flow passage 56 without departing from the scope of the present invention.

While it is contemplated the port tube 52 can have any number of layers, in a preferred form of the invention the port tube 52 will include either a discrete layer of a barrier material or a blend layer including a barrier material. The barrier material will present a barrier to the passage of gasses or water vapor transmission, and, in a preferred form of the invention, will reduce the passage rate of oxygen therethrough. It is also desirable that all materials in the solution contact layer, and more preferably all materials used in the tubing, be free of halogens, plasticizers or other low-molecular weight or water soluble components that can leach out into the solutions transferred through the tubing. Suitable barrier materials include ethylene vinyl alcohol copolymers having an ethylene content of from about 25% to about 45% by mole percent, more preferably from about 28% to about 36% by mole percent and most preferably from about 30% to about 34% by mole percent.

Figure 2A:
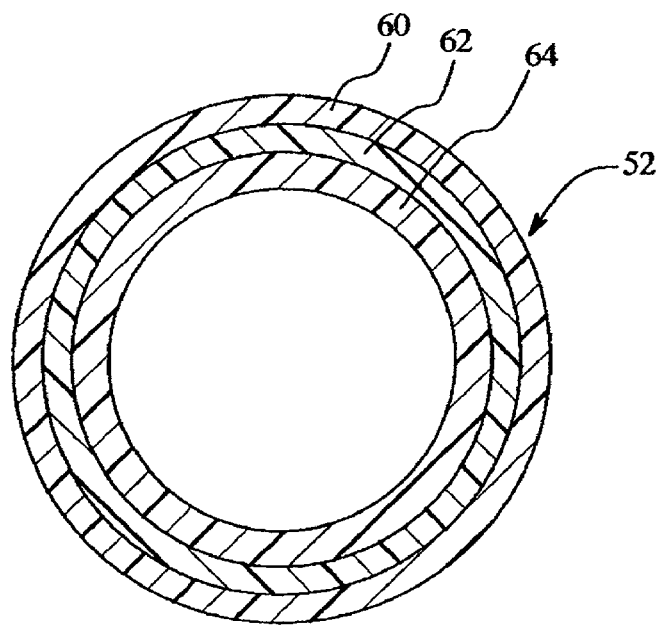
FIG. 2a is a cross-sectional view of a three-layer tubing.
Figure 2B:
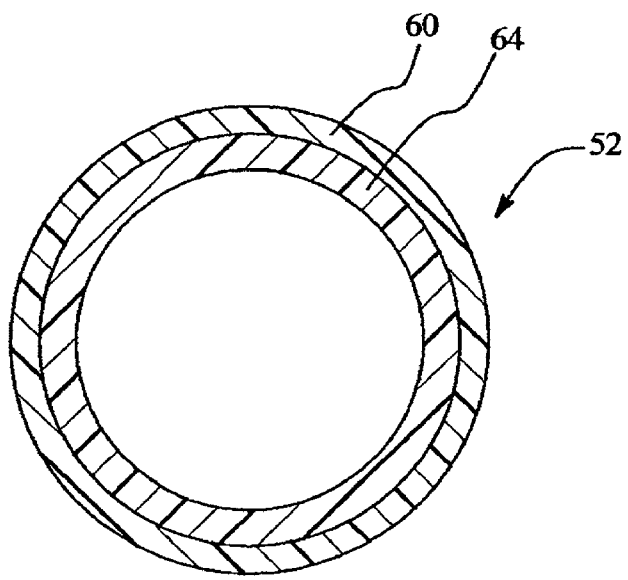
FIG. 2b is a cross-sectional view of a two-layer tubing.

In an even more preferred form of the invention, the port tube 52 will have multiple layers. FIG. 2a and FIG. 2b show respectively a three-layer port tube 52 and a two-layer port tube. The three-layer port tube 52 has an outside or an outermost layer 60, a core layer 62 and an inside solution contact layer 64. Similarly, the two-layer port tube 52 has an outside layer 60 and an inside, solution contact layer 64.

In a preferred form of the invention, the multiple layer transfer tube or port tube 52 will have a discrete layer of a barrier material with the remaining layers being selected from polyolefins. The layers of the tube can be positioned in any order, however, in a preferred form of the invention, the barrier layer is not positioned as the outside layer 60. Thus, the layers of a three layer tube can be positioned in one of six orders selected from the group: first/second/third, first/third/second, second/first/third, second/third/first, third/first/second, and third/second/first. Further, in tube embodiments having more than two layers, the tube 52 can be symmetrical or asymmetrical from a material aspect and from a thickness of layers aspect.

Suitable polyolefins include homopolymers, copolymers and terpolymers obtained using, at least in part, monomers selected from α-olefins having from 2 to 12 carbons. One particularly suitable polyolefin is an ethylene and α-olefin interpolymer (which sometimes shall be referred to as a copolymer). Suitable ethylene and α-olefin interpolymers preferably have a density, as measured by ASTM D-792 of less than about 0.915 g/cc and are commonly referred to as very low density polyethylene (VLDPE), ultra low density ethylene (ULDPE) and the like. The α-olefin should have from 3–17 carbons, more preferably from 4–12 and most preferably 4–8 carbons. In a preferred form of the invention, the ethylene and α-olefin copolymers are obtained using single site catalysts. Suitable single site catalyst systems, among others, are those disclosed in U.S. Pat. Nos. 5,783,638 and 5,272,236. Suitable ethylene and α-olefin copolymers include those sold by Dow Chemical Company under the AFFINITY trademark, Dupont-Dow under the ENGAGE trademark and Exxon under the EXACT and PLASTOMER trademarks.

The polyolefins also include modified polyolefins and modified olefins blended with unmodified olefins. Suitable modified polyolefins are typically polyethylene or polyethylene copolymers. The polyethylenes can be ULDPE, low density (LDPE), linear low density (LLDPE), medium density polyethylene (MDPE), and high density polyethylenes (HDPE). The modified polyethylenes may have a density from 0.850–0.95 g/cc. The polyethylene may be modified by grafting or otherwise chemically, electronically or physically associating a group of carboxylic acids, and carboxylic acid anhydrides. Suitable modifying groups include, for example, maleic acid, fumaric acid, itaconic acid, citraconic acid, allylsuccinic acid, cyclohex-4-ene-1,2-dicarboxylic acid, 4-methylcyclohex-4-ene-1,2-dicarboxylic acid, bicyclo[2.2.1]hept-5-ene-2,3-dicarboxylic acid, x-methylbicyclo[2.2.1]hept-5-ene-2,3-dicarboxylic acid, maleic anhydride, itaconic anhydride, citraconic anhyride, allylsuccinic anhydride, citraconic anhydride, allylsuccinic anhydride, cyclohex-4-ene-1,2-dicarboxylic anhydride, 4-methylcyclohex-4-ene-1,2-dicarboxylic anhydride, bicyclo[2.2.1]hept-5-ene2,3-dicarboxylic anhydride, and x-methylbicyclo[2.2.1]hept-5-ene-2,2-dicarboxylic anhydride.

Examples of other modifying groups include $C_1$–$C_8$ alkyl esters or glycidyl ester derivatives of unsaturated carboxylic acids such as methyl acrylate, methyl methacrylate, ethyl acrylate, ethyl methacrylate, butyl acrylate, butyl methacrylate, glycidyl acrylate, glycidal methacrylate, monoethyl maleate, diethyl maleate, monomethyl maleate, diethyl maleate, monomethyl fumarate, dimethyl fumarate, monomethyl itaconate, and diethylitaconate; amide derivatives of unsaturated carboxylic acids such as acrylamide, methacrylamide, maleicmonoamide, maleic diamide, maleic N-monoethylamide, maleic N,N-dietylamide, maleic N-monobutylamide, maleic N,N dibutylamide, fumaric monoamide, fumaric diamide, fumaric N-monoethylamide, fumaric N,N-diethylamide, fumaric N-monobutylamide and fumaric N,N-dibutylamide; imide derivatives of unsaturated carboxylic acids such as maleimide, N-butymaleimide and N-phenylmaleimide; and metal salts of unsaturated carboxylic acids such as sodium acrylate, sodium methacrylate, potassium acrylate and potassium methacrylate. More preferably, the polyolefin is modified by a fused ring carboxylic anhydride and most preferably a maleic anhydride.

The polyolefins also include ethylene vinyl acetate copolymers, modified ethylene vinyl acetate copolymers and blends thereof. The modified EVA has an associated modifying group selected from the above listed modifying groups.

In one preferred form of the invention, the tube 52 has a solution contact layer 64 of a modified EVA copolymer sold by DuPont Packaging under the trademark BYNEL® CXA, a core layer 62 of an EVOH and an outside layer 60 of a modified EVA, again preferably CXA. Such a structure is symmetrical from a materials standpoint. According to a preferred form of the invention, such tubing will have layers of the following thickness ranges: outside layer 60 from about 0.002 inches to about 0.042 inches, preferably about 0.010 inches, the core layer 62 from about 0.016 inches to about 0.056 inches, preferably about 0.039 inches, and the solution contact layer 64 of from about 0.002 inches to about 0.042 inches, preferably about 0.010 inches.

In another preferred form of the invention, the tube 52 has a solution contact layer 64 of an EVOH, a core layer 62 of a modified EVA and preferably BYNEL® CXA and an outside or outermost layer 60 of an ethylene and α-olefin copolymer. Such a structure is symmetrical from a materials standpoint. The tube layers can have various relative thicknesses. According to a preferred form of the invention, tube 52 will have layers of the following thickness ranges: outside layer 60 from about 0.002 inches to about 0.042 inches; the core layer 62 from about 0.002 inches to about 0.042 inches; and the solution contact layer 64 from about 0.016 inches to about 0.056 inches. The outermost layer 60 of EVA is well suited for bonding to the transfer tube, especially upon heat sealing.

In a further preferred form, the tube 52 has a solution contact layer 64 of BYNEL® CXA, a core layer 62 of EVOH, and an outside layer 60 of a blend of 50% ULDPE and 50% CXA. Such tubing will have layers of the following thickness ranges: outside layer 60 from about 0.002 inches to about 0.042 inches, preferably about 0.010 inches; the core layer 62 from about 0.016 inches to about 0.056 inches, preferably about 0.039 inches; and the solution contact layer 64 of from about 0.002 inches to about 0.042 inches, preferably about 0.010 inches.

In a preferred form of the invention, the port tube 52 shall have the following dimensions: inside diameter from about 0.100 inches to about 0.500 inches and the wall thickness shall be from about 0.020 inches to about 0.064 inches. The port tube 52 can be prepared by injection molding, extrusion, coextrusion or other polymer processing techniques well known in the art.

Figure 3A:
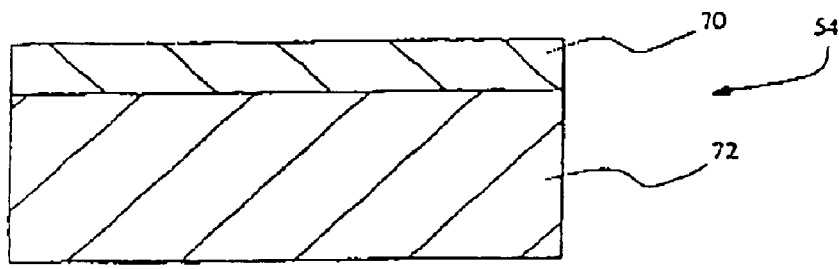
FIG. 3a is a cross-sectional view of a two-layer membrane film.
Figure 3B:
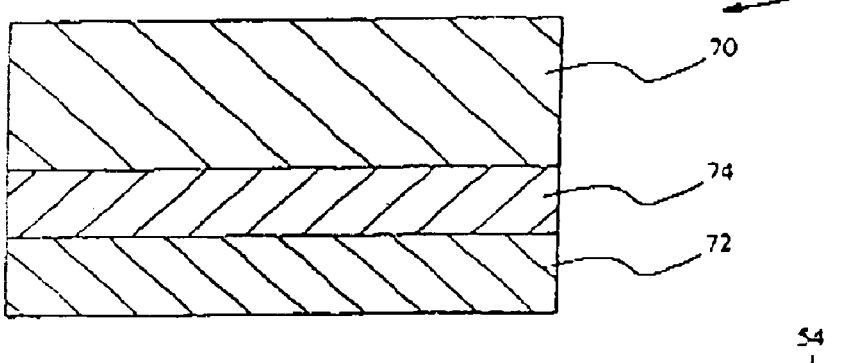
FIG. 3b is a cross-sectional view of a three-layer membrane film.
Figure 3C:
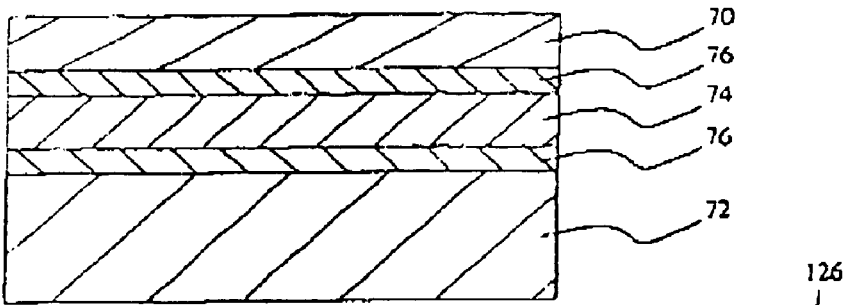
FIG. 3c is a cross-sectional view of a five-layer membrane film.

Turning our attention now to the closure 54, the membrane film forming the closure 54 can have any number of layers, but in a preferred form of the invention has multiple layers. The membrane film 54, in a preferred form of the invention, shall have a barrier layer as defined above. FIG. 3a shows a two-layer structure 54 having an outside layer 72 and an inside layer 70. FIG. 3b shows a three-layer structure 54 having an outside layer 72, an inside layer 70 and a core layer 74. FIG. 3c shows a five-layer structure 54 having an outside layer 72, an inside layer 70, a core layer 74, and two tie layers 76. In a preferred form of the invention, one layer shall be of a barrier material defined above and the remaining layer or layers shall be selected from the polyolefins defined above, polyamides and polyesters. One of the inside layer 70 or outside layer 72 shall define a tubing contact layer or seal layer.

Suitable polyamides include those obtained from a ring-opening reaction of lactams having from 4–12 carbons. This group of polyamides therefore includes, but is not limited to, nylon 6, nylon 10 and nylon 12.

Acceptable polyamides also include aliphatic polyamides resulting from the condensation reaction of di-amines having a carbon number within a range of 2–13, aliphatic polyamides resulting from a condensation reaction of di-acids having a carbon number within a range of 2–13, polyamides resulting from the condensation reaction of dimer fatty acids, and amide containing copolymers. Thus, suitable aliphatic polyamides include, for example, nylon 66, nylon 6,10 and dimer fatty acid polyamides.

Suitable polyesters include polycondensation products of di- or polycarboxylic acids and di or poly hydroxy alcohols or alkylene oxides. Preferably, the polyesters are a condensation product of ethylene glycol and a saturated carboxylic acid such as ortho or isophthalic acids and adipic acid. More preferably the polyesters include polyethyleneterephthalates produced by condensation of ethylene glycol and terephthalic acid; polybutyleneterephthalates produced by a condensations of 1,4-butanediol and terephthalic acid; and polyethyleneterephthalate copolymers and polybutyleneterephthalate copolymers which have a third component of an acid component such as phthalic acid, isophthalic acid, sebacic acid, adipic acid, azelaic acid, glutaric acid, succinic acid, oxalic acid, etc.; and a diol component such as 1,4-cyclohexanedimethanol, diethyleneglycol, propyleneglycol, etc. and blended mixtures thereof.

In a preferred form of the invention, the membrane structure shall have five layers as shown in FIG. 3c and is described in detail in commonly assigned U.S. Pat. No. 6,083,587 which is incorporated herein by reference and made a part hereof. The outside layer 72 is a polyamide and preferably nylon 12, the two tie layers 76 are a modified EVA copolymer, the core layer 74 is an EVOH and the inner layer 70 is a modified EVA. In a preferred form of the invention the inside layer 70 defines the tubing contact layer.

Further, the structure shown in FIG. 3c has the following layer thickness ranges: outside layer 72 from about 0.0005 inches to about 0.003 inches; the tie layers 76 from about 0.0005 inches to about 0.02 inches; the core layer 74 of from about 0.0005 inches to about 0.0015 inches; and an inside layer 70 of from about 0.008 inches to about 0.012 inches.

Figure 9:
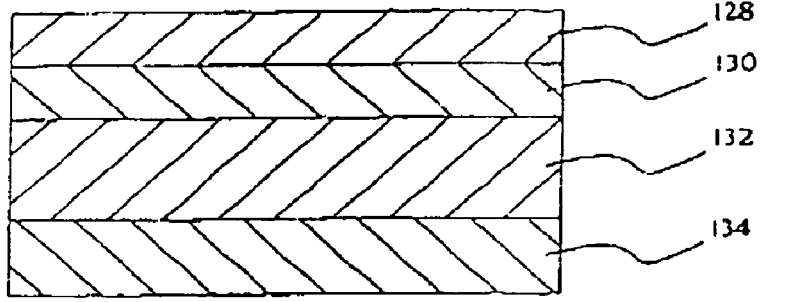
FIG. 9 is a cross-sectional view of a four-layer membrane film.

In another preferred form, the membrane structure has four layers as shown in FIG. 9. FIG. 9 shows a membrane 126 having an outer layer 128 of a polyamide, preferably nylon and more preferably a nylon 12, a third layer 130 of a modified ethylene vinyl acetate, preferably CXA, a second layer 132 of a barrier material, preferably EVOH, and an inner solution contact layer 134 of a modified ethylene vinyl acetate, preferably CXA.

The outer layer 128 has a thickness of a range of about 0.0003 to 0.0007 inches, and preferably about 0.0005 inches. The third layer 130 has a thickness range of between 0.0003 to 0.0007 inches, and preferably about 0.0005 inches. The second layer 132 has a thickness range of between 0.0007 to 0.0013 inches, and preferably about 0.001 inches. The inner layer 134 has a thickness of between 0.006 and 0.01 inches, and preferably about 0.008 inches. The membrane film can be formed by extrusion, coextrusion, lamination, extrusion coating, orother polymer processing technique well known in the art.

Turning our attention now to the receptacle 30 (FIGS. 1a, 1b and 1c). In a preferred form of the invention the receptacle 30 is of a polymeric material or structure and more preferably includes a barrier material as an additive to a layer or as a discrete barrier layer as defined above. In a preferred form of the invention, the receptacle has sidewalls 80 which are positioned in registration and sealed along a peripheral seam 82. The sealing can be carried out by conductive heat sealing or inductive heat sealing such as through radio frequency sealing or can be sealed by other methods well known in the art. The peripheral seam 82, preferably, has an outer seal 84, an inner seal 86 and a material depot 88 positioned therebetween. One or more access or administration ports 89 can be provided as is well known in the art. In a preferred form of the invention the recepatacle can have a fill port 89' on one end of the container and a administration port 89 on an opposite end of the container. The administration port can be the closure assembly 40 described above. The fill port 89' can have the same structure as the administration port or, in a more preferred form of the invention, will be of a polyolefin material, a polyolefin blend or one of the other materials set forth above but will not include the gas barrier material of the administration port. The fill port 89' can be removed after filling the container by a hot knife or during a step of sealing the container after filling. The material depot 88 defines an unsealed portion where material from the seals 84 and 86 can flow. The sidewalls 80 define a fluid containing chamber 90. The fluid chamber is capable of storing flowable materials and more preferably is capable of forming a fluid tight seal. The receptable and closure assembly will preferably have an oxygen permeability of less than 0.10 cc/day, more preferably less than 0.075 cc/day and most preferably less than 0.04 cc/day, or any range or combination of ranges therein.

In a preferred form of the invention, the sidewalls 80 are of a multiple layer structure and can include the material structures as shown in FIGS. 3a to 3c and the description set forth above for these structures. In a preferred form of the invention, the sidewall 80 has five layers. The structure is the same as that disclosed in FIG. 3c but includes an additional layer outward from inside layer 70. The inner layer is preferably a polyolefin and more preferably an ethylene and α-olefin copolymer. The relative thicknesses of the layers is fully set forth in U.S. Pat. No. 6,083,587 at column 5, line 64 through column 6, line 8.

The receptacle 30 shall have the following physical properties: modulus of elasticity of the sidewall of the receptacle is less than 60,000 psi and more preferably less than 40,000 psi; is suitable of storing an oxygen sensitive composition for at least about 6 months, more preferably at least about 1 year, more preferably at least about 2 years and even more preferably at least about 3 years; is capable of achieving these storage periods at temperatures of about room temperature and more preferably from 5° C. to about 45° C.

Turning our attention now to FIG. 4 showing a port tube/closure assembly 40. The assembly 40 preferably is constructed without the use of solvents or adhesives. The assembly 40 has one of the closure 54 described above formed into a disk shape and attached to the port tube end surface 58. The closure can also be attached inside the port tube flow passage 56. The closure 54 can be placed in contact with the end surface 58 of the port tube and attached thereto using conductive heat sealing, inductive heat sealing (such as using radio frequency energies), ultrasonic welding, vibration welding, or other techniques well known in the art.

It should be understood that a port tube 52 having any of the constructions described above can be combined with a closure 54 having any of the constructions described above. Thus, an assembly of a port tube 52 having any number of layers and a closure 54 having two layers, three layers or more is contemplated by the present invention. It is also contemplated that a port tube 52 having two layers, three layers or more could be combined with a membrane film 54 having any number of layers.

The spike holder 50 (which also may be referred to as a needle holder) is shown in FIGS. 1a, and 5–8. The spike holder 50 has a body 100 having a first annular wall defining a first cavity or chamber 110 at a first end of the body, a second annular wall defining a second cavity or a second chamber 112 at a second end of the body, and a flow passage 114 connecting the first and second chambers. The first chamber 110 is dimensioned to telescopically receive an end portion 116 of the port tube 52. In a preferred form of the invention the spike holder is fixedly attached to the port tube but could be releasably attached without departing from the scope of the present invention. It is contemplated by the present invention the annular wall could extend into the port tube flow passage 56 and attach thereto without departing from the present invention. The second chamber 112 is dimensioned to have an interference fit with an access spike or transfer needle 117 described below. As noted herein, the term interference fit means that the second chamber 112 has an identical or smaller dimension than the spike holders inserted therein but is capable of deforming (e.g., elastically) around the insert to hold the inserted device by friction. It is contemplated the second chamber 112 will fixedly attach to the insert or releasably attach to the insert. In a preferred form of the invention, the first chamber 110 and the second chamber 112 have a generally circular cross-sectional shape, the first chamber 110 having a first diameter and the second chamber 112 having a second diameter, the first diameter being larger than the second diameter.

In a preferred form of the invention, the spike holder 50 has an outwardly extending flange 118 at an intermediate portion thereof. The flange 118 is positioned generally at the intersection of the first chamber 110 and the second chamber 112. The flange 118 has a first surface 120 which is textured to facilitate handling and manipulation of the holder. In one embodiment, this texture is provided by a plurality of buttresses 122 around the first annular wall of the body 100. In a preferred form of the invention, the flange 118 is generally circular in cross-sectional shape and the buttresses 122 are circumferentially spaced about the first surface 120. The buttresses are shown having a generally tear-drop shape, however, they could be of numerous different shapes without departing from the present invention. The buttresses are provided to form a gripping surface for those handling the spike holder 50. It may also be desirable to add an internal shoulder or other feature to the spike holder 50 to limit the extent the transfer tube can be inserted into the flow passage.

The spike holder 50 is formed from a polyolefin as defined above and more particularly is an ethylene and α-olefin copolymer. The spike holder 50 can also have a textured or matte finish on a portion or the entire outer surface 124 of the holder 50 for ease of handling. The spike holder 50 can be formed by any suitable polymer forming technique known to those skilled in the art and preferably the spike holder 50 is formed by injection molding. The spike holder 50 can also include a membrane film 54' positioned in the passageway 114 in lieu of or in addition to the membrane 54.

In a preferred form of the invention, the spike holder 50 is formed directly over the end portion 116 of the port tube/membrane film assemblies 40 described above. Such a process is conventional and referred to as an overmolding process. The overmolding process includes the steps of: (1) providing a tubing as set forth above; providing a mold for forming a spike holder; inserting a portion 116 of the tubing 52 into the mold; and supplying polymeric material to the mold to form a spike holder on the tubing.

In an embodiment of the invention, the tubing, closure, and/or container sidewalls are comprised of a multilayer polymeric structure which includes a first layer of an ethylene vinyl alcohol copolymer having first and second sides, and a second layer of a modified ethylene vinyl acetate copolymer attached to the first side of the first layer. The second layer has a thickness of greater than 1.2 mils, preferably at least 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 mils. The polymeric structure optionally includes a third layer attached to the second side of the first layer. Preferably, the third layer comprises a polyamide or polyester as described herein. In one embodiment, the sidewalls of a container include a core layer, outside layer, or solution contact layer comprising a modified ethylene vinyl acetate copolymer as described herein. In another embodiment, the polymeric structure comprises an outside layer of a polyamide or polyester, a core layer of an ethylene vinyl alcohol copolymer, and a sealing layer of a modified ethylene vinyl acetate copolymer, wherein the core layer is between the outside and sealing layers. This polymeric structure optionally includes one or more tie layers attached to the core layer.

The receptacles of the present invention are used to store deoxyhemoglobin solutions or other therapeutic fluids which react with oxygen. The receptacles are filled with the solution in a low oxygen or oxygen free environment, sealed, and then stored at about 5 to 45° C. for weeks or months prior to use. Conventional methods of filling and sealing containers in a low oxygen or oxygen free environment are suitable for the invention. After storage, the deoxyhemoglobin solution contains less than 15% methemoglobin and is physiologically acceptable for administration to a patient. In a preferred embodiment, the deoxyhemoglobin solutions are stored at room temperature and ambient conditions.

The following is an example of the present invention and is not intended to limit the claims of the present invention.

EXAMPLE

Several 250 ml volume receptacles were fabricated as shown in FIG. 1c with a fill port and an administration port. Each receptacles had a total nominal surface area of approximately 450 cm$^2$. The administration port had a core layer of an EVOH and an outside layer of a modified EVA (CXA) and a solution contact layer of a modified EVA (CXA). A membrane film was sealed to a distal end of the administration port. The membrane had an outer layer 134 of nylon 12, a third layer 130 of a modified ethylene vinyl acetate (CXA), a second layer 132 of EVOH, and an inner solution contact layer 128 of a modified ethylene vinyl acetate (CXA) (see FIG. 9). The fill port was injection molded of ethylene vinyl acetate (EVA). The receptacle sidewalls were fabricated from a five-layer structure as shown in FIG. 3c.

An outside layer 72 was nylon 12, two tie layers 76 were a modified EVA copolymer (CXA), a core layer 74 was an EVOH and the inner layer 70 was a metallocene catalyzed ultra low density polyethylene. The empty containers were sterilized by exposure to gamma radiation. The sterile containers were aseptically filled with an oxygen sensitive indicator solution through the fill port and the fill port was sealed and removed by a heated bar. The oxygen permeability of the containers were measured at 70% relative humidity at temperatures of 4° C., 23° C. and 40° C. and found to be 0.0008, 0.0041, and 0.0396 cc/day/package, respectively.

It is understood that, given the above description of the embodiments of the invention, various modifications may be made by one skilled in the art. Such modifications are intended to be encompassed by the claims below.

What is claimed is:

1. A receptacle for a medical fluid susceptible to deterioration on exposure to a gas such as oxygen or carbon dioxide, said receptacle comprising:
   walls of sheet material each including at least one layer forming a barrier essentially impermeable to said gas;
   a seal sealing the walls together in a region thereof;
   a transfer tube sealed in the seal having a proximal end in the receptacle, a distal end accessible from outside the receptacle, a flow passage extending between said proximal and distal ends, the tube having a layer including an ethylene vinyl alcohol copolymer; and
   a closure blocking flow through said flow passage adapted to be pierced by a tubular needle for transfer of medical fluid through the needle, said transfer tube and closure being essentially impermeable to said gas.

2. A receptacle as set forth in claim 1 wherein said closure is attached to a distal end surface of the transfer tube.

3. A receptacle as set forth in claim 2 wherein the closure is a multiple layer polymeric structure.

4. A receptacle as set forth in claim 3 wherein the multiple layer polymeric structure comprises:
   a first layer of an ethylene vinyl alcohol copolymer having a first side and a second side; and
   a second layer of a modified ethylene vinyl acetate copolymer attached to the first side of the first layer.

5. A receptacle as set forth in claim 4 further comprising a third layer attached to the second side of the first layer.

6. A receptacle as set forth in claim 5 wherein the third layer is selected from the group consisting of polyamides and polyesters.

7. A receptacle as set forth in claim 6 wherein the polyamides are aliphatic polyamides obtained from the condensation reaction of di-amines having a carbon number within a range of 2–13, aliphatic polyamides resulting from a condensation reaction of di-acids having a carbon number within a range of 2–13, polyamides resulting from the condensation reaction of dimer fatty acids, and amide containing copolymers.

8. A receptacle as set forth in claim 7 wherein the polyamide is obtained from a ring-opening reaction of a lactam.

9. A receptacle as set forth in claim 4 wherein the modified ethylene vinyl acetate copolymer has a modifying group selected from the group consisting of: carboxylic acid and carboxylic acid anhydrides.

10. A receptacle as set forth in claim 9 wherein the modifying group is selected from the group consisting of: maleic acid, fumaric acid, itaconic acid, citraconic acid, allylsuccinic acid, cyclohex-4-ene-1,2-dicarboxylic acid, 4-methylcyclohex-4-ene-1,2-dicarboxylic acid, bicyclo[2.2.1]hept-5-ene-2,3-dicarboxylic acid, x-methylbicyclo[2.2.1]hept-5-ene-2,3-dicarboxylic acid, maleic anhydride, itaconic anhydride, citraconic anhyride, allylsuccinic anhydride, citraconic anhydride, allylsuccinic anhydride, cyclohex-4-ene-1,2-dicarboxylic anhydride, 4-methylcyclohex-4-ene-1,2-dicarboxylic anhydride, bicyclo[2.2.1]hept-5-ene2,3-dicarboxylic anhydride, and x-methylbicyclo[2.2.1]hept-5-ene-2,2-dicarboxylic anhydride, methyl acrylate, methyl methacrylate, ethyl acrylate, ethyl methacrylate, butyl acrylate, butyl methacrylate, glycidyl acrylate, glycidal methacrylate, monoethyl maleate, diethyl maleate, monomethyl maleate, diethyl maleate, monomethyl fumarate, dimethyl fumarate, monomethyl itaconate, and diethylitaconate; amide derivatives of unsaturated carboxylic acids such as acrylamide, methacrylamide, maleicmonoamide, maleic diamide, maleic N-monoethylamide, maleic N,N-dietylamide, maleic N-monobutylamide, maleic N,N dibutylamide, fumaric monoamide, fumaric diamide, fumaric N-monoethylamide, fumaric N,N-diethylamide, fumaric N-monobutylamide and fumaric N,N-dibutylamide; imide derivatives of unsaturated carboxylic acids such as maleimide, N-butymaleimide and N-phenylmaleimide; and metal salts of unsaturated carboxylic acids such as sodium acrylate, sodium methacrylate, potassium acrylate and potassium methacrylate.

11. A receptacle as set forth in claim 10 wherein the modifying group is a fused ring carboxylic acid anhydride.

12. A receptacle as set forth in claim 4 wherein the second layer is positioned between the first layer of ethylene vinyl alcohol and the end of the tubing.

13. A receptacle as set forth in claim 12 wherein the ethylene vinyl alcohol copolymer has an ethylene content of from about 25% to about 45% by mole percent.

14. A receptacle as set forth in claim 12 wherein the ethylene vinyl alcohol copolymer has an ethylene content of from about 28% to about 36% by mole percent.

15. A receptacle as set forth in claim 12 wherein the ethylene vinyl alcohol copolymer has an ethylene content of from about 30% to about 34% by mole percent.

16. A receptacle as set forth in claim 1 having a needle holder on the distal end of the transfer tube.

17. A receptacle as set forth in claim 16 wherein said layers comprise an inside layer of heat sealable material having an inner face and an outer face, said barrier layer being superposed on the outer face of said inside layer.

18. The receptacle as set forth in claim 16 wherein said barrier layer comprises ethylene vinyl alcohol.

19. A receptacle as set forth in claim 1 wherein each of said walls comprises multiple superposed layers at least one of which constitutes said barrier layer.

20. A receptacle as set forth in claim 1 wherein said transfer tube comprises multiple superposed layers comprising:
   a first layer of ethylene vinyl alcohol copolymer;
   a second layer;
   a third layer;
   wherein the second layer and the third layer each being selected from the group consisting of: (1) ethylene and α-olefin interpolymers having a density of less than about 0.915 g/cc, (2) ethylene vinyl acetate copolymers, and (3) modified ethylene vinyl acetate copolymers; and
   wherein the first layer, the second layer and the third layer are concentrically disposed with respect to one another.

21. A receptacle as set forth in claim 20 wherein the second layer is a first α-olefin interpolymer.

22. A receptacle as set forth in claim 21 wherein the third layer is a modified ethylene vinyl acetate copolymer.

23. A receptacle as set forth in claim 22 wherein the modified ethylene vinyl acetate copolymer has a modifying group selected from carboxylic acid and carboxylic acid anhydrides.

24. A receptacle as set forth in claim 23 wherein the modifying group is selected from the group consisting of: maleic acid, fumaric acid, itaconic acid, citraconic acid, allylsuccinic acid, cyclohex-4-ene-1,2-dicarboxylic acid, 4-methylcyclohex-4-ene-1,2-dicarboxylic acid, bicyclo[2.2.1]hept-5-ene-2,3-dicarboxylic acid, x-methylbicyclo[2.2.1]hept-5-ene-2,3-dicarboxylic acid, maleic anhydride, itaconic anhydride, citraconic anhyride, allylsuccinic anhydride, citraconic anhydride, allylsuccinic anhydride, cyclohex-4-ene-1,2-dicarboxylic anhydride, 4-methylcyclohex-4-ene-1,2-dicarboxylic anhydride, bicyclo[2.2.1]hept-5-ene2,3-dicarboxylic anhydride, and x-methylbicyclo[2.2.1]hept-5-ene-2,2-dicarboxylic anhydride, methyl acrylate, methyl methacrylate, ethyl acrylate, ethyl methacrylate, butyl acrylate, butyl methacrylate, glycidyl acrylate, glycidal methacrylate, monoethyl maleate, diethyl maleate, monomethyl maleate, diethyl maleate, monomethyl fumarate, dimethyl fumarate, monomethyl itaconate, and diethylitaconate; amide derivatives of unsaturated carboxylic acids such as acrylamide, methacrylamide, maleicmonoamide, maleic diamide, maleic N-monoethylamide, maleic N,N-dietylamide, maleic N-monobutylamide, maleic N,N dibutylamide, fumaric monoamide, fumaric diamide, fumaric N-monoethylamide, fumaric N,N-diethylamide, fumaric N-monobutylamide and fumaric N,N-dibutylamide; imide derivatives of unsaturated carboxylic acids such as maleimide, N-butymaleimide and N-phenylmaleimide; and metal salts of unsaturated carboxylic acids such as sodium acrylate, sodium methacrylate, potassium acrylate and potassium methacrylate.

25. A receptacle as set forth in claim 24 wherein the modifying group is a fused ring carboxylic acid anhydride.

26. A receptacle as set forth in claim 21 wherein the third layer is a second α-olefin interpolymer.

27. A receptacle as set forth in claim 26 wherein the second α-olefin has from 2 to 12 carbons.

28. A receptacle as set forth in claim 26 wherein the second α-olefin has from 4 to 8 carbons.

29. A receptacle as set forth in claim 21 wherein the first α-olefin has from 2 to 12 carbons.

30. A receptacle as set forth in claim 21 wherein the first α-olefin has from 4 to 8 carbons.

31. A receptacle as set forth in claim 21 wherein the second layer is a first ultra-low density polyethylene.

32. A receptacle as set forth in claim 31 wherein the first ultra-low density polyethylene is obtained using a catalyst type selected from the group consisting of: vanadium, metallocene, single site, Ziegler-Natta and modified Ziegler-Natta.

33. A receptacle as set forth in claim 32 wherein the catalyst type is metallocene.

34. A receptacle as set forth in claim 32 wherein the catalyst type is single site.

35. A receptacle as set forth in claim 1 wherein the transfer tube is relatively rigid and the closure comprises a puncturable wall adjacent the distal end of the transfer tube.

36. A transfer tube for attachment to a receptacle adapted to hold a medical fluid susceptible to deterioration on exposure to gas such as oxygen or carbon dioxide, said transfer tube comprising a tubular body having a proximal end, a distal end opposite the proximal end, a flow passage extending between said proximal and distal ends adapted to communicate with said receptacle, and a closure blocking flow through the flow passage and adapted to be pierced by a tubular needle for transfer of medical fluid through the needle, said tubular body and closure being essentially impermeable to said gas and each having a layer including an ethylene vinyl alcohol copolymer.

37. A transfer tube as set forth in claim 36 wherein said transfer tube comprises multiple superposed layers comprising:
    a first layer of ethylene vinyl alcohol copolymer;
    a second layer;
    a third layer;
    wherein the second layer and the third layer each being selected from the group consisting of: (1) ethylene and α-olefin interpolymers having a density of less than about 0.915 g/cc, (2) ethylene vinyl acetate copolymers, and (3) modified ethylene vinyl acetate copolymers; and
    wherein the first layer, the second layer and the third layer are concentrically disposed with respect to one another.

38. A transfer tube as set forth in claim 37 wherein the first α-olefin has from 4 to 8 carbons.

39. A transfer tube as set forth in claim 38 wherein the second layer is a first ultra-low density polyethylene.

40. A transfer tube as set forth in claim 39 wherein the first ultra-low density polyethylene is obtained using a catalyst type selected from the group consisting of: vanadium, metallocene, single site, Ziegler-Natta and modified Ziegler-Natta.

41. A transfer tube as set forth in claim 40 wherein the catalyst type is single site.

42. A transfer tube as set forth in claim 40 wherein the catalyst type is metallocene.

43. A transfer tube as set forth in claim 37 wherein the third layer is a second α-olefin interpolymer.

44. A transfer tube as set forth in claim 43 wherein the second α-olefin has from 2 to 12 carbons.

45. A transfer tube as set forth in claim 43 wherein the second α-olefin has from 4 to 8 carbons.

46. A transfer tube as set forth in claim 37 wherein the third layer is a modified ethylene vinyl acetate copolymer.

47. A transfer tube as set forth in claim 37 wherein the first α-olefin has from 2 to 12 carbons.

48. A transfer tube as set forth in claim 37 wherein the second layer is a first α-olefin interpolymer.

49. A transfer tube as set forth in claim 36 having a needle holder on the distal end of the tubular body.

50. A transfer tube as set forth in claim 49 wherein said tubular body is formed from multiple superposed layers at least one of which is a barrier layer essentially impermeable to said gas.

51. A transfer tube as set forth in claim 36 wherein the tubular body is relatively rigid and the closure comprises an end wall of puncturable material essentially impermeable to said gas on the distal end of the body.

52. A method for storing a medical fluid susceptible to deterioration on exposure to gas, the method comprising:
    providing a container comprising walls of sheet material each including at least one layer forming a barrier essentially impermeable to said gas; a seal sealing the walls together in a region thereof; a transfer tube sealed in the seal having a proximal end in the container, a distal end accessible from outside the container, a flow passage extending between said proximal and distal ends, the tube having a layer including an ethylene vinyl alcohol copolymer; and a closure blocking flow through said flow passage adapted to be pierced by a tubular needle for transfer of therapeutic through the needle, said transfer tube and closure being essentially impermeable to said gas;

filling the container with the medical fluid; and storing the filled container at 5 to about 45 degrees Centigrade for at least about 6 months.

53. The method of claim 52 wherein the medical fluid is deoxyhemoglobin.

54. The method of claim 52 wherein the filled container is stored at room temperature for about one year.

55. A method for storing a medical fluid susceptible to deterioration on exposure to gas, the method comprising:

providing a container comprising walls of sheet material each including at least one first layer of ethylene vinyl alcohol and at least one second layer of modified ethylene vinyl acetate copolymer, said second layer having a thickness of more than 1.2 mils, and said sheet material forming a barrier essentially impermeable to said gas; a seal sealing the walls together in a region thereof; a transfer tube sealed in the seal having a proximal end in the container, a distal end accessible from outside the container, a flow passage extending between said proximal and distal ends; and a closure blocking flow through said flow passage adapted to be pierced by a tubular needle for transfer of medical fluid through the needle, said transfer tube and closure being essentially impermeable to said gas;

filling the container with the medical fluid; and storing the filled container at 5 to about 45 degrees Centigrade for at least about 6 months.

56. A receptacle for a medical fluid susceptible to deterioration on exposure to a gas such as oxygen or carbon dioxide, said receptacle comprising:

walls of sheet material each including at least one first layer of ethylene vinyl alcohol and at least one second layer of modified ethylene vinyl acetate copolymer, said second layer having a thickness of more than 1.2 mils, and said sheet material forming a barrier essentially impermeable to said gas;

a seal sealing the walls together in a region thereof;

a transfer tube sealed in the seal having a proximal end in the receptacle, a distal end accessible from outside the receptacle, a flow passage extending between said proximal and distal ends; and a closure blocking flow through said flow passage adapted to be pierced by a tubular needle for transfer of medical fluid through the needle, said transfer tube and closure being essentially impermeable to said gas.

* * * * *